US009771545B2

(12) United States Patent
Gayral Chirac et al.

(10) Patent No.: US 9,771,545 B2
(45) Date of Patent: Sep. 26, 2017

(54) HYDROTROPIC AGENT, USE THEREOF TO MAKE NON-IONIC SURFACTANTS SOLUBLE, AND COMPOSITIONS CONTAINING SAME

(75) Inventors: Marie-Francoise Gayral Chirac, Viviers-les-Montagnes (FR); Sebastien Kerverdo, Vincennes (FR); Jerome Guilbot, Castres (FR); Herve Rolland, Castres (FR)

(73) Assignee: SOCIETE D'EXPLOITATION DE PRODUITS POUR LES INDUSTRIES CHEMIQUES SEPPIC, Paris (FR)

( * ) Notice: Subject to any disclaimer, the term of this patent is extended or adjusted under 35 U.S.C. 154(b) by 1131 days.

(21) Appl. No.: 13/989,586

(22) PCT Filed: Nov. 14, 2011

(86) PCT No.: PCT/FR2011/052635
§ 371 (c)(1),
(2), (4) Date: May 24, 2013

(87) PCT Pub. No.: WO2012/069730
PCT Pub. Date: May 31, 2012

(65) Prior Publication Data
US 2013/0247942 A1 Sep. 26, 2013

(30) Foreign Application Priority Data
Nov. 25, 2010 (FR) ...................................... 10 59762

(51) Int. Cl.
| C11D 1/66 | (2006.01) |
| C07H 15/04 | (2006.01) |
| B08B 3/04 | (2006.01) |
| C11D 1/825 | (2006.01) |
| C08L 71/02 | (2006.01) |

(52) U.S. Cl.
CPC ............... *C11D 1/662* (2013.01); *B08B 3/04* (2013.01); *C07H 15/04* (2013.01); *C08L 71/02* (2013.01); *C11D 1/825* (2013.01)

(58) Field of Classification Search
CPC ............ C11D 1/662; C11D 1/825; C11D 1/72
See application file for complete search history.

(56) References Cited

U.S. PATENT DOCUMENTS

| 5,205,959 A * | 4/1993 | Schmid ................ C11D 1/8255 510/219 |
| 5,681,938 A | 10/1997 | Boiteux et al. |
| 6,015,839 A | 1/2000 | Milius |
| 6,300,298 B1 | 10/2001 | Milius et al. |
| 6,541,442 B1 * | 4/2003 | Johansson ............... C11D 1/662 134/25.2 |
| 6,583,102 B2 * | 6/2003 | Milius ................ B01F 17/0092 510/238 |
| 7,534,760 B2 * | 5/2009 | Johansson ............... C11D 1/662 134/25.2 |
| 9,080,132 B2 * | 7/2015 | Gayral Chirac ....... C11D 1/825 |
| 2008/0039666 A1 | 2/2008 | Grothe et al. |
| 2012/0245070 A1 * | 9/2012 | Eskuchen .............. C11D 1/662 510/218 |
| 2013/0247942 A1 * | 9/2013 | Gayral Chirac ....... C07H 15/04 134/26 |
| 2014/0113850 A1 * | 4/2014 | Gayral Chirac ....... C11D 1/825 510/109 |
| 2016/0010027 A1 * | 1/2016 | Bauer .................... C11D 1/825 510/365 |

FOREIGN PATENT DOCUMENTS

| FR | 2111966 | 6/1972 |
| FR | 2754739 | 4/1998 |
| JP | 04-124196 | 4/1992 |
| JP | H05-500074 | 1/1993 |
| JP | H08-509702 | 10/1996 |
| JP | H11-503784 | 3/1999 |
| JP | 2001-521057 | 11/2001 |

(Continued)

OTHER PUBLICATIONS

JP Office Action, dated Sep. 8, 2015; Application No. 2013-540421.
Adasch et al., "Preparation of alkyl alpha- and -Beta-D-glucopyranosides, thermotropic properties and X-ray analysis," Carbohydrate Research, 314 (3-4), 2005, pp. 177-187.
Berger et al., "Relating Surfactant Properties to Activity and Solubilization of the Human Adenosine A3 Receptor," Biophysical Journal, vol. 89, Jul. 2005, pp. 452-464.
Dahlhoff,"Amphiphilic carbohydrate-based mesogens; I. Mesogenic O-n-alkyl beta.-D-mannofuranosides: synthesis of a novel homologous series of glycosides," Synthesis 1987, pp. 366-368.
De Bruyne et al., "Acid hydrolysis of alkyl beta-D-galactopyranosides," Carbohydrate Research, 25 (1), 1972, pp. 59-65.

*Primary Examiner* — Gregory Webb
(74) *Attorney, Agent, or Firm* — Young & Thompson

(57) ABSTRACT

A compound having Formula (I), $nC_7$—$H_{15}$—O-$(G)_p$-H, where G is a reducing sugar residue, and p is a decimal number ≥1.05 and ≤5. The method for preparing the compound and its use as a hydrotropic surfactant by making soluble, in an aqueous alkaline composition, at least one non-ionic surfactant having Formula (II), R—(O—CH(R')—CH2)n-(O-CH2-CH2)m-0-H, where R is a straight, branched, saturated or unsaturated aliphatic hydrocarbon radical including 8-14 carbon atoms, R' is a methyl or ethyl radical, n and m are whole numbers ≥0 and ≤15, assuming that n+m≥0. Cleaning compositions containing 0.5% to 20% of compounds of Formula (I), 0.5% to 80% of compounds of Formula (II), 10-50 wt % of at least one alkaline agent, 15-89 wt % of water, and optionally, 10-50 wt % of at least one anti-limescale agent are useful for cleaning hard surfaces.

2 Claims, No Drawings

(56) References Cited

FOREIGN PATENT DOCUMENTS

| JP | 2009-102267 | 5/2009 | |
|---|---|---|---|
| SE | WO 9921948 A1 * | 5/1999 | ............ C11D 1/662 |
| WO | 91-03538 | 3/1991 | |
| WO | 91-14760 | 10/1991 | |
| WO | 96-33255 | 10/1996 | |
| WO | 99-21948 | 5/1999 | |
| WO | 2005-085321 | 9/2005 | |

* cited by examiner

HYDROTROPIC AGENT, USE THEREOF TO MAKE NON-IONIC SURFACTANTS SOLUBLE, AND COMPOSITIONS CONTAINING SAME

The present invention relates to a novel surfactant, to the use thereof as a hydrotropic agent, in particular for making soluble nonionic active surfactants which are low foaming in aqueous compositions that are stable in a concentrated alkaline medium, in particular used for cleaning.

Hydrotropic agents are chemical substances which are used to make soluble chemical compounds which have low solubility or are insoluble in water or in aqueous phases of compositions comprising them. The expression "chemical compounds which have low solubility or are insoluble in water or in aqueous phases" denotes compounds which, when added to a phase predominantly or totally made up of water do not make it possible to obtain a solution or a composition which is totally clear, transparent, isotropic, homogeneous and stable at a desired temperature for a desired period of time. This lack of solubility is in particular due to the chemical structure of the compound in question and/or to the presence of alkaline agents and/or of electrolytes and/or of neutral salts in the aqueous phase in which it is desired to make said compound soluble.

Among the compounds which have low solubility or are insoluble in water, mention may be made of hydrophobic compounds, for instance oils, essential oils, fragrances, pigments, anionic surfactants, cationic surfactants, nonionic surfactants and amphoteric surfactants.

Hydrotropic agents are particularly used for preparing cosmetic compositions, pharmaceutical compositions, cleaning compositions intended for the detergence of hard surfaces for household or industrial applications, or compositions used for oil operations containing brines.

The cosmetic compositions requiring the use of hydrotropic agents are generally compositions in which the formulator wishes to make soluble oils and/or essential oils and/or fragrances and/or surfactants in the presence of a large amount of neutral salts and/or of electrolytes.

The cleaning compositions intended for the detergence of hard surfaces for household or industrial applications, for instance cleaning bottles, washing floors or cleaning metal surfaces soiled with fats, comprise detergent surfactants and also a high concentration of alkaline agents so as to increase the cleaning effectiveness of said compositions. These compositions must not generate the formation of a considerable foam during the cleaning operation in the presence of the dirt to be treated, and must show good wetting properties and also good detergent power in an alkaline medium.

Owing to their amphiphilic structure, the detergent surfactants used in cleaning compositions intended for the detergence of hard surfaces for household or industrial applications gives said compositions their ability to remove the dirt present on hard surfaces and to keep it in suspension so that it can then be removed during the rinsing step. These detergent surfactants may be of anionic, cationic, amphoteric or nonionic nature. Nonionic surfactants are particularly used for the preparation of detergent compositions for hard surfaces given their foaming power which is generally lower than the other ionic surfactants and also their improved environmental characteristics. Since these cleaning compositions comprise large amounts of electrolytes, introduced via the alkaline agents and via water-softening agents, for instance sequestering agents and/or ion exchangers and/or precipitating agents, it is difficult to dissolve large amounts of detergent surfactants in order to obtain a stable composition which does not show storage deposits.

In order to improve the solubility of chemical compounds which have low solubility or are insoluble in water or in aqueous phases, it is known to those skilled in the art to use hydrotropic agents, for instance organic solvents such as ethanol, xylene sulfonates and cumene sulfonates. Ethanol is an effective hydrotropic agent, but it has the drawback of bringing dangers of explosiveness. Xylene sulfonates and cumene sulfonates are not very effective for large amounts of surfactants and do not exhibit biodegradability properties required in order to conform to the new environmental regulations either.

Alkylpolyglycosides are also described as agents for making defoaming nonionic surfactants soluble.

International publication WO 96/33255A1 describes antifoam compositions comprising a particular alkylpolyglucoside, the alkyl chain of which is constituted by the 2-ethylhexyl radical, and defoaming nonionic surfactants chosen from those comprising one or more groups chosen from monoethoxylated or polyethoxylated groups, and monopropoxylated or polypropoxylated groups. It is taught therein that alkylpolyglucosides comprising a 2-ethylhexyl chain are more effective than alkylpolyglycosides comprising a hexyl chain for making defoaming nonionic surfactants soluble.

International publication WO 99/21948A1 discloses compositions which are clear and stable at high alkaline concentrations, the foaming powers of which are controlled, containing a large amount of alkylene oxide-based nonionic surfactants and a hexylglycoside as hydrotropic agent. These compositions are characterized by a good wetting capacity and good detergent properties for hard surfaces. It is taught therein that hexylglycosides, and more particularly n-hexylpolyglucoside, make it possible to make nonionic surfactants soluble in strongly alkaline media and that n-hexylglucoside is characterized by a higher solubilizing capacity than 2-ethylhexyl glucoside and than Exxal 7 glucoside in the presence of amounts of sodium hydroxide of between 10% and 40% for a nonionic surfactant of which the structure results from the ethoxylation, with 4 mol of ethylene oxide, of a mixture of linear and branched alcohols, with a content of linear alcohols of approximately 80%, comprising from 9 to 11 carbon atoms. However, neither 2-ethyl-hexylglucoside or n-hexylglucoside are characterized by properties which make it possible to make soluble both a large amount of alkaline agent and a large amount of electrolytes introduced via water-softening agents.

The applicant has therefore endeavored to develop a novel technical solution, consisting of a new hydrotropic agent which makes it possible more particularly to prepare compositions comprising nonionic detergent surfactants and has nonecotoxic and biodegradable and noninflammable characteristics, making it possible to make soluble compounds which have low solubility or are insoluble in water, and more particularly to make nonionic surfactants soluble in an aqueous medium in the presence of a high content of alkaline agent and/or of electrolytes and/or of neutral salts. Consequently, according to a first aspect, a subject of the invention is a compound of formula (I):

$$n\text{C}_7\text{H}_{15}\text{—O-(G)}_p\text{-H} \quad (I)$$

in which G represents the residue of a reducing sugar, and p represents a decimal number greater than or equal to 1.05 and less than or equal to 5, or a mixture of said compounds of formula (I).

In the definition of the compound of formula (I) as previously defined, p is a decimal number which represents the average degree of polymerization of the residue G. When p is an integer, (G)$_p$ is the polymeric residue of rank p of the G residue. When p is a decimal number, formula (I) represents a mixture of compounds:

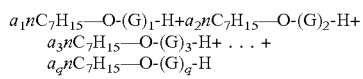
$a_1 nC_7H_{15}$—O-(G)$_1$-H+$a_2 nC_7H_{15}$—O-(G)$_2$-H+
$a_3 nC_7H_{15}$—O-(G)$_3$-H+ . . . +
$a_q nC_7H_{15}$—O-(G)$_q$-H with q representing an integer between 1 and 5 and in the molar proportions $a_1, a_2, a_3, \ldots a_q$ such that:

$$\sum_{q=5}^{q=1} a_q = 1; a_1 > 0$$

The term "reducing sugar" denotes, in formula (I), the saccharide derivatives which do not have in their structures a glycosidic linkage established between an anomeric carbon and the oxygen of an acetal group, as they are defined in the reference book: "Biochemistry", Daniel Voet/Judith G. Voet, p. 250, John Wyley & Sons, 1990. The oligomeric structure (G)$_p$ can be in any of the isomer forms, whether this is optical isomerism, geometric isomerism or positional isomerism; they can also represent a mixture of isomers.

In formula (I) as defined above, the $nC_7H_{15}$—O group is bonded to G via the anomeric carbon of the saccharide residue, so as to form an acetal function.

According to one particular aspect of the present invention, in the definition of the compounds of formulae (I), G represents the residue of a reducing sugar chosen from glucose, dextrose, sucrose, fructose, idose, gulose, galactose, maltose, isomaltose, maltotriose, lactose, cellobiose, mannose, ribose, xylose, arabinose, lyxose, allose, altrose, dextran or tallose.

According to one particular aspect of the present invention, in the definition of the compounds of formula (I), G represents the residue of a reducing sugar chosen from glucose, xylose and arabinose residues, and p represents a decimal number greater than or equal to 1.05 and less than or equal to 2.5.

According to an even more particular aspect of the present invention, in the definition of the compounds of formula (I), G represents the residue of a reducing sugar chosen from glucose, xylose and arabinose residues, and p represents a decimal number greater than or equal to 1.05 and less than or equal to 2.0, and even more particularly greater than or equal to 1.25 and less than or equal to 2.0.

According to a second aspect, a subject of the invention is a process for preparing the compound of formula (I) or the mixture of said compounds of formula (I) as previously defined, comprising the following successive steps;
a step A) of reacting a reducing sugar of formula (III):

HO-(G)$_p$-H          (III)

in which G represents the residue of a reducing sugar, with a molar excess of n-heptanol of formula $nC_7H_{15}$—OH, so as to form a mixture of compounds of formula (I) as previously defined and of n-heptanol;
a step B) of removing the n-heptanol from said mixture obtained in step A).

Step A) is generally carried out in a reactor in the presence of an acidic catalytic system, by controlling the stoichiometric ratio between the two reagents, and more particularly by introducing a molar excess of n-heptanol, and with mechanical stirring under predetermined temperature and partial vacuum conditions, for example at a temperature of between 70° C. and 130° C. and under a partial vacuum of between 300 mbar (3×10$^4$ Pa) and 20 mbar (2×10$^3$ Pa). The term "acidic catalytic system" denotes strong acids such as sulfuric acid, hydrochloric acid, phosphoric acid, nitric acid, hypophosphorous acid, methanesulfonic acid, (para-toluene)sulfonic acid or (trifluoro-methane)sulfonic acid, or ion exchange resins.

Step B) of removing the n-heptanol from said mixture obtained at the end of step A) is generally carried out according to methods known to those skilled in the art, for instance distillation, thin film distillation, molecular distillation or solvent extraction.

Such a preparation process can be finished off, if necessary or if desired, by neutralization, filtration or discoloration operations.

According to another aspect, a subject of the invention is the use of a compound of formula (I) or of the mixture of compounds of formula (I) as previously defined, as a hydrotropic surfactant.

The expression "hydrotropic surfactant" denotes a surfactant which makes it possible to make soluble compounds which have low solubility or are insoluble in the aqueous phase of a composition, by mixing said hydrotrophic surfactant and the compound to be made soluble in the aqueous phase of a composition.

The expression "compounds which have low solubility or are insoluble in water" denotes compounds which, when added to a phase predominantly or totally made up of water and in the presence of alkaline agents and/or of electrolytes and/or of neutral salts, does not make it possible to obtain a solution or a composition which is clear, transparent, isotropic, homogeneous and stable at the desired temperature. Among these compounds which have low solubility or are insoluble in water, mention may, for example, be made of oils, essential oils, fragrances, pigments, anionic surfactants, cationic surfactants, nonionic surfactants and amphoteric surfactants. Among the neutral salts, mention may be made of ammonium chloride, alkali metal salts, for instance sodium chloride, sodium sulfate and sodium nitrate, and alkaline-earth metal salts, for instance calcium chloride.

The compounds of formula (I) or the mixture of compounds of formula (I) used as hydrotropic surfactants which are subjects of the present invention and as previously defined can be incorporated into cosmetic, dermocosmetic, dermopharmaceutical or pharmaceutical compositions, or industrial or household detergence compositions.

According to another aspect, a subject of the invention is the use of the compound of formula (I) as previously defined, as an agent for making soluble, in an aqueous alkaline composition, at least one nonionic surfactant of formula (II):

R—(O—CH(R')—CH$_2$)$_n$(O—CH$_2$—CH$_2$)$_m$O—H          (II)

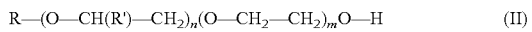

in which R represents a linear or branched, saturated or unsaturated, hydrocarbon-based aliphatic radical comprising from 8 to 14 carbon atoms, R' represents a methyl or ethyl radical, n represents an integer greater than or equal to 0 and less than or equal to 15, m represents an integer greater than or equal to 0 and less than or equal to 15, it being understood that the sum n+m is greater than zero.

The expression "aqueous alkaline composition" denotes any aqueous composition which has a pH value greater than 7.

The expression "linear or branched, saturated or unsaturated, hydrocarbon-based aliphatic radical comprising from 8 to 14 carbon atoms, optionally substituted with one or more hydroxyl groups" denotes, for the R radical in formula (II) as defined:
- linear alkyl radicals, for example n-octyl, n-decyl, n-dodecyl or n-tetradecyl radicals;
- radicals derived from isoalkanols of formula (1):

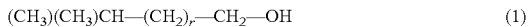
$$(CH_3)(CH_3)CH-(CH_2)_r-CH_2-OH \qquad (1)$$

in which r represents an integer between 4 and 10, for example isooctyl, isononyl, isodecyl, isoundecyl, isododecyl, isotridecyl or isotetradecyl radicals;
- the 2-ethylhexyl radical or branched alkyl radicals derived from Guerbet alcohols of formula (2):

$$CH(C_sH_{2s+1})(C_tH_{2t+1})-CH_2-OH \qquad (2)$$

in which t is an integer between 4 and 10, s is an integer between 2 and 10 and the sum s+t is greater than or equal to 6 and less than or equal to 12, for example 2-ethyldecyl, 2-butyloctyl, 2-ethyldodecyl, 2-butyldecyl, 2-hexyloctyl, 2-butyldecyl or 2-hexyloctyl radicals; or radicals derived from the homologs of Guerbet alcohols, for example the 2-propylheptyl radical;
- radicals derived from branched alcohols of formula (3):

$$CH_3-[CH(R'')]_z-CH_2-OH \qquad (3)$$

in which R" represents a hydrogen atom or a methyl radical, and z represents an integer greater than or equal to 3 and less than or equal to 15;
- unsaturated linear radicals, such as undecenyl, dodecenyl or tetradecenyl radicals, for instance the 10-undecenyl, 4-dodecenyl or 5-dodecenyl unsaturated radicals;
- linear or branched, saturated or unsaturated aliphatic radicals comprising from 8 to 14 carbon atoms, substituted with one or two hydroxyl groups, such as hydroxyoctyl, hydroxydecyl or hydroxydodecyl radicals, for example the 8-hydroxyoctyl, 10-hydroxydecyl or 12-hydroxydodecyl radicals.

According to one particular aspect of the present invention, a subject thereof is the use of a compound of formula (I) for making soluble, in an alkaline composition, at least one nonionic surfactant of formula (II) as previously defined, in which the R radical represents a radical chosen from octyl, decyl, dodecyl, tetradecyl, 2-ethylhexyl, 2-butyloctyl, 2-butyldecyl, 2-hexyloctyl, isooctyl, isononyl, isodecyl, isoundecyl, isododecyl, isotridecyl, isotetradecyl or 2-propylheptyl radicals.

According to one more particular aspect of the present invention, a subject thereof is the use of a compound of formula (I) for making soluble, in an alkaline composition, at least one nonionic surfactant of formula (II) as previously defined, in which n represents an integer greater than or equal to 0 and less than or equal to 6, more particularly greater than or equal to 0 and less than or equal to 3, and even more particularly greater than or equal to 0 and less than or equal to 2.

According to one more particular aspect of the present invention, a subject thereof is the use of a compound of formula (I) for making soluble, in an alkaline composition, at least one nonionic surfactant of formula (II) as previously defined, in which m represents an integer greater than or equal to 1 and less than or equal to 9, more particularly greater than or equal to 2 and less than or equal to 4.

The compounds of formula (II) for which R' represents a methyl or ethyl radical and n represents an integer greater than or equal to 1 are prepared according to a process comprising, if necessary, a step a) of alkoxylation by reacting n molar equivalents of an alkylene oxide or of an alkylene carbonate with one molar equivalent of alcohol of formula (IV):

$$R-OH \qquad (IV)$$

in which the R radical represents a linear or branched, saturated or unsaturated, hydrocarbon-based aliphatic radical comprising from 8 to 14 carbon atoms, optionally substituted with one or more hydroxyl groups, as defined above, so as to obtain the alkoxylated alcohol of formula (V):

$$R-(O-CH(R')-CH_2)_n-O-H \qquad (V)$$

in which R' represents a methyl or ethyl radical; and/or, if necessary, a step b) of ethoxylation by reacting one molar equivalent of the alkoxylated alcohol of formula (V) obtained at the end of step a) with m molar equivalents of ethylene oxide or of ethylene carbonate.

In step a) of the process for preparing the compounds of formula (II) as described above, the alkylene oxide is chosen from the elements of the group made up of propylene oxide and butylene oxide, and the alkylene carbonate is chosen from the elements of the group made up of propylene carbonate and butylene carbonate.

The compounds of formula (II) for which n is equal to 0 are prepared according to a process implementing a step a') of ethoxylation by reacting m molar equivalents of ethylene oxide or of ethylene carbonate with the alcohol of formula (IV) as defined above.

In the processes described above, n and m represent the integers described above in the definition of the compounds of the formula (II).

The alkoxylation reaction of step a) and the ethoxylation reactions of steps a') and b), as defined above, are generally carried out in a reactor in the presence of a basic catalyst, such as alkali metal hydroxides, for instance sodium hydroxide or potassium hydroxide, alkali metal alkoxides, for instance sodium methoxide or potassium methoxide, sodium tert-butylate or potassium tert-butylate, Lewis bases, for instance triphenylphosphine, or coordination catalysts, for instance cobalt- and/or zinc-based organometallic complexes, or in the presence of an acid catalyst, such as a Lewis acid, for instance boron trifluoride, aluminum trichloride or tin tetrachloride.

Such processes for preparing the compounds of formula (II) can be finished off, if necessary and if desired, with neutralization, demineralization, filtration and discoloration operations.

According to another particular aspect of the present invention, a subject thereof is the use of a compound of formula (I) for making at least one nonionic surfactant of formula (II) as defined above soluble in an aqueous alkaline composition in which the weight ratio between the compound of formula (I) and the compound of formula (II) is less than or equal to 9/1 and greater than or equal to 1/4.

According to another more particular aspect of the present invention, a subject thereof is the use of a compound of formula (I) for making at least one nonionic surfactant of formula (II) as defined above soluble in an aqueous alkaline composition in which the weight ratio between the compound of formula (I) and the compound of formula (II) is less than or equal to 4/1 and greater than or equal to 1/4, more particularly less than or equal to 3/1 and greater than or equal to 1/3, and even more particularly less than or equal to 2/1 and greater than or equal to 1/2.

According to another aspect, a subject of the invention is a composition ($C_1$) comprising, for 100% of its weight:

a) from 0.5% to 20% by weight, more particularly from 0.5% to 15% by weight, and even more particularly from 0.5% to 10% by weight of at least one compound of the formula (I), as defined above;

b) from 0.5% to 80% by weight, more particularly from 0.5% to 50% by weight, and even more particularly from 0.5% to 35% by weight of at least one nonionic surfactant of formula (II):

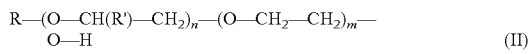

(II)

in which R represents a linear or branched, saturated or unsaturated, hydrocarbon-based aliphatic radical comprising from 8 to 14 carbon atoms, R' represents a methyl or propyl radical, n represents an integer greater than or equal to 0 and less than or equal to 15, m represents an integer greater than or equal to 0 and less than or equal to 15, it being understood that the sum n+m is greater than zero;

c) from 10% to 50% by weight, more particularly from 20% to 50% by weight and even more particularly from 20% to 50% by weight of at least one alkaline agent chosen from the elements of the group made up of alkali metal hydroxides or alkaline-earth metal hydroxides;

d) from 15% to 89% by weight, more particularly from 15% to 50% by weight, and even more particularly from 20% to 50% by weight of water; and, optionally e) from 10% to 50% by weight, more particularly from 20% to 50% by weight, and even more particularly from 30% to 50% by weight of at least one water softening agent.

In the composition ($C_1$) which is subject of the present invention, the alkaline agents are chosen from the elements of the group made up of alkali metal hydroxides or alkaline-earth metal hydroxides, for instance sodium hydroxide, potassium hydroxide, barium hydroxide and calcium hydroxide.

According to an even more particular aspect, in the composition ($C_1$) which is the subject of the present invention, the alkaline agent is chosen from the elements of the group consisting of sodium hydroxide and potassium hydroxide.

In the composition ($C_1$) which is a subject of the present invention, the optional water softening agent is chosen from the elements of the group made up of sequestering agents, for instance sodium tripolyphosphate (TPP), ethylenediaminetetraacetate (EDTA), tetraacetylethylenediamine (TAED), methyl glycine diacetate (MGDA), sodium nitrilotriacetate ($Na_3NTA$), sodium gluconate, potassium gluconate, sodium erythorbate, potassium erythorbate, sodium polycarboxylate, potassium polycarboxylate and sodium citrate, of ion exchange agents, for instance sodium zeolites or aluminosilicates, or lamellar sodium silicates, precipitating agents, for instance calcium carbonate and sodium metasilicate.

The sequestering agents, and more particularly the sequestering agents described above, have the effect of complexing the calcium and magnesium ions so as to form water-soluble complexes which are subsequently removed during rinsing.

The ion exchange agents, and more particularly the ion exchange agents described above, have the effect of exchanging their sodium ions with calcium and magnesium ions.

The precipitating agents, and more particularly the sequestering agents described above, have the effect of removing the ions responsible for the hardness of the water by forming insoluble calcium compounds, which are subsequently removed with the dirt on the cleaned surfaces.

According to a more particular aspect, in the composition ($C_1$) which is the subject of the present invention, the optional water softening agent is chosen from the elements of the group consisting of sodium metasilicate, sodium tripolyphosphate (TPP), ethylenediaminetetraacetate (EDTA), tetraacetylethylenediamine (TAED), methyl glycine diacetate (MGDA), sodium nitrilotriacetate ($Na_3NTA$), sodium gluconate, sodium citrate and calcium carbonate.

According to one particular aspect, in the composition ($C_1$) which is the subject of the present invention, the weight ratio between the compound of formula (II) and the compound of formula (I) is less than or equal to 9/1 and greater than or equal to 1/4, more particularly less than or equal to 4/1 and greater than or equal to 1/4, more particularly less than or equal to 3/1 and greater than or equal to 1/3, and even more particularly less than or equal to 2/1 and greater than or equal to 1/2.

According to another aspect, a subject of the invention is the use of a composition ($C_1$) as defined above for cleaning hard surfaces.

The expression "for cleaning hard surfaces" denotes any action intended to enable the removal of dirt present on surfaces consisting of various materials. The surfaces to be cleaned can be hard surfaces or textile surfaces. The term "hard surfaces" denotes, for example, floors, walls, window panes, tiles, household electrical appliances, crockery, worktops, faucets, sinks, storage tanks for chemical, food or agricultural products, vehicles (automobiles, motorcycles, trucks, etc.).

The materials constituting these hard surfaces are, for example, glass (soda-lime glass, calcium fluoride glass, borosilicate glass, crystal), porcelain, earthenware, ceramic, polycarbonate plastics, polypropylenes, stainless steel, silver, copper, aluminum, wood, synthetic resins, vitreous ceramic, and linoleum, and can be coated with paints or varnishes.

As an example of dirt present on these hard surfaces and which is to be removed by cleaning, mention may be made, for example, of food residues, fats, heavy and light hydrocarbons, burnt residues, dust, sludge, finger marks, soap residues and microorganisms.

The composition ($C_1$) which is the subject of the present invention is in particular in the form of a solution, an emulsion or a microemulsion comprising an aqueous continuous phase, an emulsion or a microemulsion comprising an oily continuous phase, a gel, a foam, or else in the form of an aerosol.

The composition ($C_1$) which is the subject of the present invention can be applied directly by sprinkling or by spraying on the surface to be cleaned or else by means of any type of support intended to be brought into contact with the hard surface to be cleaned (paper, wipe, textile) comprising said composition ($C_1$).

The composition ($C_1$) which is a subject of the present invention, used for cleaning hard surfaces, generally has a pH greater than 9, preferably greater than 11, and more particularly greater than 13.

Generally, the composition ($C_1$) which is a subject of the present invention also comprises ingredients normally used in the field of cleaning hard surfaces, such as nonionic surfactants, cationic surfactants, cationic polymers, thickeners, enzymes, bleaching agents, anticorrosion agents, preservatives, fragrances, dyes or repellents.

As examples of nonionic surfactants present in the composition ($C_1$) which is a subject of the present invention, mention may be made of:

block copolymers of ethylene oxide and of propylene oxide, and most particularly the block copolymers of ethylene oxide and of propylene oxide that are sold under the brand name Pluronic™ by the company BASF, for instance Pluronic™ PE 6100 and Pluronic™ PE 6200;

defoaming nonionic surfactants of formula ($A_1$):

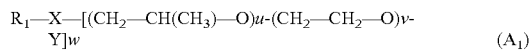

$$R_1-X-[(CH_2-CH(CH_3)-O)u-(CH_2-CH_2-O)v-Y]w \quad (A_1)$$

in which:

$R_1$ represents a linear or branched, saturated or unsaturated, hydrocarbon-based aliphatic radical comprising from 6 to 18 carbon atoms, X represents a nitrogen atom or an oxygen atom, v represents an integer between 1 and 50, u represents an integer between 1 and 50, w represents an integer equal to 1 if X represents an oxygen atom, and w represents an integer equal to 1 or 2 if X represents a nitrogen atom, Y represents a blocking functional group chosen from the elements of the group made up of linear alkyl radicals comprising from 4 to 8 carbon atoms, for instance the butyl radical, the benzyl radical, or a butylene oxide group.

Among the defoaming nonionic surfactants of formula ($A_1$), mention may be made of the products sold under the brand name Tergitol™ by the company Dow Chemical, for instance Tergitol™ L61E and Tergitol™ L64E;

low-foaming nonionic surfactants of formula ($A_2$):

$$R_2-O-(S)_q-H \quad (A_2)$$

in which:

S represents the residue of a reducing sugar chosen from the elements of the group made up of glucose, xylose and arabinose, $R_2$ represents a linear or branched, saturated hydrocarbon-based radical comprising from 6 to 10 carbon atoms, q represents a decimal number greater than or equal to 1.05 and less than or equal to 5.

As examples of low-foaming nonionic surfactants of formula ($A_2$) present in the composition ($C_1$) which is a subject of the present invention, mention may be made of hexylpolyglucosides and 2-ethylpolyglucosides.

As examples of thickeners present in the composition ($C_1$) which is a subject of the present invention, mention may be made of polymeric thickeners, such as polycarboxylates having a molecular weight of between 500 000 and 4 000 000 grams per mol, more particularly between 1 000 000 and 4 000 000 grams per mol, with a degree of crosslinking of between 0.5 mol % and 4 mol %, such as those sold under the trade names Carbopol™, Acrysol™ ICS-1 and Sokalan™. The preferred polycarboxylates are polyacrylates of copolymers of acrylic acid with ethylene, with propylene or maleic acid.

As examples of thickeners present in the composition ($C_1$) which is a subject of the present invention, mention may be made of polymeric thickeners such as acrylamide homopolymers, or copolymers of acrylamide and of the sodium salt of 2-acrylamido-2-methylpropane-sulfonate, for instance the thickeners sold by the company SEPPIC under the brand name Solagum™.

As examples of thickeners present in the composition ($C_1$) which is a subject of the present invention, mention may be made of inorganic thickeners, for instance clays, montmorillonite (or bentonite), volkonskoite, smectite, nontronite, beidellite, hectorite, saponite, sauconite or vermiculite.

The thickeners present in the composition ($C_1$) which is a subject of the present invention are used in amounts of between 0.1% and 10% by weight.

As examples of abrasive agents present in the composition ($C_1$) which is a subject of the present invention, mention may be made of materials of natural origin, for instance wood or nut shavings, inorganic abrasive materials, such as oxides, carbonates, quartzes, diatomaceous earths, or colloidal silica dioxides, organic abrasive materials, such as polyolefins, for instance polyethylenes and polypropylenes, polyesters, polystyrenes, acetonitrile-butadiene-styrene resins, melamines, polycarbonates, phenolic resins, epoxy resins and polyurethane resins.

The abrasive agents present in the composition ($C_1$) which is a subject of the present invention are used in amounts of between 5.0% and 30% by weight.

As examples of enzymes present in the composition ($C_1$) which is the subject of the present invention, mention may be made of proteases, lipases and amylases.

As examples of bleaching agents present in the composition ($C_1$) which are subjects of the present invention, mention may be made of sodium hypochlorite, peroxygenated compounds, for instance calcium percarbonate, and perborates.

According to another aspect, the subject of the invention is a process for cleaning a hard surface comprising at least one step $a_1$) of applying the composition ($C_1$) as defined above to said hard surface, followed by at least one step $b_1$) of rinsing said hard surface.

In step $a_1$) of the cleaning process which is a subject of the invention, the composition ($C_1$) is applied to the surface comprising the dirt to be cleaned by any means, for example in an open bath, by sprinkling, or by application via a support consisting of synthetic or natural, woven or nonwoven textile fibers, or of paper, preimpregnated with said composition ($C_1$).

In step $b_1$) of the cleaning process which is a subject of the invention, the rinsing of the hard surface to which the composition ($C_1$) was applied during step $a_1$) is carried out in an open bath or by sprinkling of water.

Step $b_1$) of the cleaning process which is the subject of the invention can be carried out at ambient temperature or at a temperature of between 30° C. and 80° C., more particularly at a temperature of between 30° C. and 65° C.

The following examples illustrate the invention without, however, limiting it.

1) Preparation of Compounds of Formula (I) which are Subjects of the Invention and Evaluation of their Surfactant Properties 1.1) Preparation of n-heptylpolyglucosides 2.7 molar equivalents of n-heptanol are introduced into a double-jacketed glass reactor, in which a heat-transfer fluid circulates, and which is equipped with an efficient stirrer, at a temperature of 40° C. One molar equivalent of anhydrous glucose is then gradually added to the reaction medium so as to allow it to be homogeneously dispersed, and then 0.15% by mass of 98% sulfuric acid and 0.15% by mass of 50% hypophosphorous acid for 100% of the weight made up by the sum of the weight of the glucose and of the weight of the n-heptanol are introduced into the previously prepared homogeneous dispersion. The reaction medium is placed under a partial vacuum of approximately 180 mbar, and kept at a temperature of 100° C.-105° C. for a period of 4 hours with removal of the water formed by means of a distillation setup. The reaction medium is then cooled to 85° C.-90° C. and neutralized by adding 40% sodium hydroxide so as to bring the pH of a 5% solution of this mixture to a value of approximately 7.0. The resulting reaction medium is then emptied out at a temperature of 70° C. and filtered in order to remove the grains of glucose which have not reacted. The filtrate is then introduced into a double-jacketed glass reactor, in which a heat-transfer fluid circulates, equipped with an efficient stirrer and a distillation device. The excess heptanol is then removed by distillation at a temperature of 120° C. under a partial vacuum of between approximately 100 mbar and 50 mbar. The reaction medium thus distilled is immediately diluted by adding an amount of water so as to reach a concentration of reaction medium of approximately 60%. After homogenization for 30 minutes at a temperature of 50° C., the composition ($X_0$) obtained is emptied out.

The analytical characteristics of the resulting composition ($X_0$) comprising n-heptylpolyglucosides are collated in table 1 below.

TABLE 1

Analytical characteristics of the composition ($X_0$)

| | Composition ($X_0$) |
|---|---|
| Appearance at 20° C. (visual determination) | liquid |
| Acid number (standard NFT 60204) | 1.7 |
| Hydroxyl number on dry extract (standard USP XXI NF XVI 01/01/1995) | 813.9 |
| Water (% by weight) (standard NFT 73201) | 58.8% |
| Residual content of n-heptanol (gas chromatography) as % by weight | 0.22% |

1.2) Evaluation of the Foaming Properties of n-heptylpolyglucosides

The foaming properties of the composition ($X_0$) of n-heptylpolyglucosides, obtained according to the process previously described, were evaluated according to a static method by nitrogen bubbling and compared with solubilizing compositions of the prior art, namely:

- the composition of n-hexylpolyglucosides which is sold under the brand name AG 6206 by the company Akzo Nobel (composition $X_1$),
- the composition of 2-ethylhexylpolyglucosides which is sold under the brand name AG 6202 by the company Akzo Nobel (composition $X_2$),
- the composition of n-octylpolyglucosides/n-decylpolyglucosides which is sold under the brand name Simulsol™ SL8 (composition $X_3$) by the company SEPPIC,
- the sodium cumene sulfonate (composition $X_4$) which is sold under the brand name Eltesol™ SC Pellets by the company IMCD France.

1.2.1) Principle of the Static Method by Nitrogen Bubbling for Evaluating the Foaming Power The foam is formed by introducing a predetermined volume of nitrogen into a solution of surfactant at fixed concentration and in the presence of a fixed amount of sodium hydroxide, at a specific temperature. The volume of foam generated by introducing the volume of nitrogen is measured at the end of the introduction of said volume of nitrogen, and then at a time of 30 seconds, then of 120 seconds following the end of the introduction of the volume of nitrogen.

1.2.2) Experimental Protocol

5 $cm^3$ of a solution at 5 g/l, with respect to dry extract, of the compositions tested are introduced into a thermostatically controlled 250 $cm^3$ graduated measuring cylinder along with an amount of 12.5 grams of sodium hydroxide. The measurements were carried out at 20° C. and 60° C. A gas dispensing finger with a porosity of 3 (ref. Corning Pyrex 853-1) is positioned in such a way that the end of the sintered nozzle is one centimeter from the bottom of the measuring cylinder. The nitrogen flow rate is then precisely adjusted to 50 l/h and sparging is carried out for 15 seconds. After this period of time, the delivery of nitrogen is halted and the experimenter records the initial foam volume and also the foam volume after 30 seconds and 120 seconds. At least two tests producing equivalent results were carried out in different measuring cylinders for one and the same surfactant solution.

1.2.3) Expression of the Results

The results of the foam volume observed in the graduated measuring cylinder initially, and then at 30 seconds and at 120 seconds are expressed in $cm^3$.

1.2.4) Characterization of the Foaming Power of the Composition ($X_0$) Comprising the Compounds of Formula (I) According to the Invention Compared with that of the Compositions ($X_1$), ($X_2$), ($X_3$) and ($X_4$) Comprising the Prior Art Compounds 1.2.4.1) Results Obtained The experimental protocol described in section 1.2.2 of the present application was carried out for the composition of n-heptylpolyglucosides (composition $X_0$) obtained according to the process described in section 1.1 of the present application, and for the compositions ($X_1$), ($X_2$), ($X_3$) and ($X_4$) previously described.

The experimental measurements were carried out at two different temperatures: at 20° C. and at 60° C. for each of the compounds described above.

The experimental measures, for each composition and at each temperature, were recorded at the end of the introduction of the volume of nitrogen (t=0), 30 seconds after the end of the introduction of the volume of nitrogen (t=30 s) and 120 seconds after the end of the introduction of the volume of nitrogen (t=120 s), and were set down in tables 2 and 3 below for the measurements carried out respectively at 20° C. and at 60° C.

TABLE 2

Foaming power at 20° C.

| | | Composition | | | | |
|---|---|---|---|---|---|---|
| | | ($X_0$) | ($X_1$) | ($X_2$) | ($X_3$) | ($X_4$) |
| Foam volume (in $cm^3$) | At t = 0 | 100 | 65 | 120 | 125 | 65 |
| | At t = 30 s | 5 | 5 | 90 | 110 | 5 |
| | At t = 120 s | 0 | 0 | 50 | 100 | 0 |

TABLE 3

Foaming power at 60° C.

| | | Composition | | | | |
|---|---|---|---|---|---|---|
| | | ($X_0$) | ($X_1$) | ($X_2$) | ($X_3$) | ($X_4$) |
| Foam volume (in $cm^3$) | At t = 0 | 10 | 30 | 70 | 140 | 45 |
| | At t = 30 s | 5 | 1 | 30 | 120 | 1 |
| | At t = 120 s | 0 | 0 | 10 | 110 | 0 |

1.2.4.2. Analysis of the Results

The composition ($X_0$) which is a subject of the present invention is characterized by the generation of a foam which is very unstable at 20° C. since the foam volume decreases in 30 seconds by 95% of its initial value, compared with 92.3% for the composition ($X_1$), 25% for the composition ($X_2$) and 12% for the composition ($X_3$).

At 60° C., the composition ($X_0$) of n-heptylpolyglucosides which is a subject of the present invention is also characterized by the generation of a foam which is very unstable since the foam volume decreases in 30 seconds by 100% of its initial value, compared with 57.1% for the composition ($X_2$) and 14% for the composition ($X_3$). At 60° C., the composition ($X_0$) by the generation of a foam volume which is less than that generated by the prior art compositions.

1.3) Evaluation of the Wetting Properties of n-heptylpolyglucosides

The wetting properties of the composition ($X_0$) of n-heptylpolyglucosides, obtained according to the process previously described, were evaluated according to an evaluation method on a cotton disk, adapted from standards ISO 8022, 1990 edition, and NFT 73420.

1.3.1) Principle of the Method on Cotton Disk for Evaluating Wetting Power

The object of this method is to determine the wettability of a surfactant compared with a textile support, in this case raw cotton. The wetting power is assessed by the measurement of the duration of wetting of a disk of raw cotton placed in a solution of surfactants at a defined concentration, in the presence of a defined amount of sodium hydroxide.

1.3.2) Experimental Protocol 700 cm³ of a solution at 5 g/l, with respect to dry extract, of the compounds tested, in distilled water, are placed in a beaker which is thermostatically controlled at the desired temperature in the presence of 35 grams of sodium hydroxide. A disk of raw cotton corresponding to standard NFT 73-406 (30 mm in diameter) and provided by the company Mortelecque, is introduced into the previously prepared solution using immersion tongs specific to this test. The duration of wetting is determined experimentally using a stopwatch started at the moment the lower part of the disk touches the solution and stopped at the moment the disk sinks by itself into the solution, so as to obtain a duration of wetting. Ten consecutive measurements of the duration of wetting were carried out with the same solution for each composition, care being taken, however, to discard the cotton disks used after each measurement.

1.3.3)—Expression of the Results

The wetting power is expressed by a duration $t_m$ in seconds corresponding to the mean of the ten measurements carried out for each of the compositions tested.

1.3.4) Characterization of the Wetting Power of the Composition ($X_0$) Comprising the Compounds of Formula (I) According to the Invention Compared with that of the Compositions ($X_1$), ($X_2$), ($X_3$) and ($X_4$) Comprising the Prior Art Compounds 1.3.4.1.) Results Obtained The experimental protocol described in section 1.3.2 of the present application was carried out for the composition of n-heptylpolyglucosides (composition $X_0$) obtained according to the process described in section 1.1 of the present application, and for the compositions ($X_1$), ($X_2$), ($X_3$) and ($X_4$) previously described.

The experimental measurements were carried out at two different temperatures: at 20° C. and at 60° C. for each of the compositions described above.

The experimental measurements of the durations of wetting $t_m$, measured for each composition at 20° C. and at 60° C., were recorded and set out in table 4.

TABLE 4

Wetting power at 20° C. and at 60° C.

| | | Composition | | | | |
|---|---|---|---|---|---|---|
| | | ($X_0$) | ($X_1$) | ($X_2$) | ($X_3$) | ($X_4$) |
| Wetting power on cotton disk (expressed as duration of wetting | at 20° C. | >300 s | >300 s | 25 s | 11 s | >300 s |
| | at 60° C. | 155 s | >300 s | 49 | 23 s | >300 s |

1.3.4.2) Analysis of the Results

At 20° C., the composition ($X_0$) of n-heptylpolyglucosides which is a subject of the present invention is characterized by a low wetting power, identical to that of the composition ($X_1$) and to that of the composition ($X_4$), but lower than those of the compositions ($X_2$) and.

At 60° C., the wetting power of the composition ($X_0$) is better, while that of the compositions ($X_1$) and ($X_4$) remains low and those of the compositions ($X_2$) and ($X_3$) are decreased.

1.4) Evaluation of the Solubilizing Properties of n-heptylpolyglucosides in Sodium Medium The solubilizing properties, in a sodium medium, of the composition ($X_0$) of n-heptylpolyglucosides, obtained according to the process previously described, were evaluated in comparison with the prior art compositions ($X_1$), ($X_2$), ($X_3$) and ($X_4$) as previously described, according to the methods of evaluation described below for various nonionic surfactants and at various concentrations of sodium hydroxide.

1.4.1—Evaluation of the Solubilizing Power in a Sodium Medium for Several Weight Ratios of Surfactants to be made Soluble/Solubilizing Composition 1.4.1.1—Principle of the Method The object of this method is to determine the solubilizing power of a surfactant composition in a sodium medium for a nonionic surfactant insoluble in a sodium medium which is fixed, compared with surfactant compositions of the prior art.

1.4.1.2—Experimental Protocol

An amount of one gram of a nonionic surfactant (Ti) to be made soluble, an amount of $x_1$ gram of the solubilizing surfactant composition (Xi) to be tested, an amount of $y_1$ grams of sodium hydroxide and an amount of distilled water to make up the volume to obtain a solution of 100 cm³ are introduced into a 120 cm³ glass flask. A magnetized magnetic bar is placed in the glass flask, which is then magnetically stirred at a speed of 100 revolutions/minute for a period of 1 hour at a temperature of 20° C.

1.4.1.3—Expression of the Results

The visual appearance of the solution obtained according to the protocol of section 1.4.1.2 of the present application is noted by the experimenter and described as "clear" or "cloudy", as appropriate.

1.4.1.4—Characterization of the Solubilizing Power in a Sodium Medium of the Composition ($X_0$) Comprising the Compounds of Formula (I) According to the Invention Compared with that of the Compositions ($X_1$), ($X_2$), ($X_3$) and ($X_4$) Comprising the Prior Art Compounds Results Obtained The experimental protocol described in section 1.4.1.2 of the present application was carried out for the composition ($X_0$) according to the invention and for the solubilizing prior art surfactant compositions ($X_1$), ($X_2$), ($X_3$) and ($X_4$).

The experimental protocol described in section 1.4.2. of the present application was carried out for the following nonionic surfactants (Ti):

composition of polyethoxylated alcohols (T1), sold under the brand name Simulsol™ OX1004L by the company SEPPIC, resulting from the reaction of one molar equivalent of an alcohol sold under the brand name Exxal™ 10 (CAS number: 68526-85-2) by the company Exxonmobil, comprising a mixture of n-nonanol, n-decanol, n-undecanol, isononanol, isodecanol and isoundecanol, with 4 molar equivalents of ethylene oxide, composition of polyethoxylated alcohols (T2), sold under the brand name Simulsol™ OX1006L by the company SEPPIC, resulting from the reaction of one molar equivalent of an alcohol sold under the brand name Exxal™ 10 (CAS number: 68526-85-2) by the company Exxonmobil, comprising a mixture of n-nonanol, n-decanol, n-undecanol, isononanol, isodecanol and isoundecanol, with 6 molar equivalents of ethylene oxide, composition of polyethoxylated alcohols (T3), sold under the brand name Simulsol™ OX1309L by the company SEPPIC, resulting from the reaction of one molar equivalent of an alcohol sold under the brand name Exxal™ 13 (CAS number: 68256-86-3) by the company Exxonmobil, comprising a mixture of n-undecanol, n-dodecanol, n-tridecanol, n-tetradecanol, isoundecanol, isododecanol and isotridecanol, with 9 molar equivalents of ethylene oxide, composition of polyethoxylated alcohols (T4), prepared by reaction between 1 molar equivalent of n-decanol and 4 molar equivalents of ethylene oxide in the presence of potassium hydroxide as basic catalyst.

The experimental measurements were carried out in the presence of different amounts $y_1$ of sodium hydroxide so as to obtain weight contents of 10%, 20%, 30% and 48% for each of the amounts $x_1$ of the various solubilizing compositions $(X_0)$, $(X_1)$, $(X_2)$, $(X_3)$ and $(X_4)$ tested, and for each of the nonionic surfactants (T1), (T2), (T3) and (T4) described above. The amount $x_1$ of the various solubilizing compositions $(X_0)$, $(X_1)$, $(X_2)$, $(X_3)$ and $(X_4)$ tested is determined so as to achieve weight ratios of composition (Ti)/compositions (Xi)(Ti/Xi) equal to 1/1 to 1/2 and to 1/5.

The appearances of the solutions prepared by carrying out the operating protocol for each of the compositions $(X_0)$, $(X_1)$, $(X_2)$, $(X_3)$ and $(X_4)$ used to make the compositions (T1), (T2), (T3) and (T4) soluble were noted by the experimenter and set out respectively in tables 5, 6, 7 and 8 below.

TABLE 5

Appearance of solutions comprising the nonionic surfactant composition (T1) in the presence of the compositions $(X_0)$, $(X_1)$, $(X_2)$, $(X_3)$ and $(X_4)$ at 20° C. (Cle: Clear; Clo: Cloudy)

| | | | | Appearance of the compositions | | | | |
|---|---|---|---|---|---|---|---|---|
| | | | | $X_0$ | $X_1$ | $X_2$ | $X_3$ | $X_4$ |
| Amount by weight of sodium hydroxide (% by weight) | 10% | Weight ratio (T1/Xi) | 1/1 | Cle | Clo | Clo | Cle | Clo |
| | | | 1/2 | Cle | Cle | Cle | Cle | Cle |
| | | | 1/5 | Cle | Cle | Cle | Cle | Cle |
| | 20% | Weight ratio (T1/Xi) | 1/1 | Cle | Clo | Clo | Clo | Clo |
| | | | 1/2 | Cle | Cle | Cle | Clo | Clo |
| | | | 1/5 | Cle | Cle | Cle | Cle | Clo |
| | 48% | Weight ratio (T1/Xi) | 1/1 | Cle | Clo | Clo | Clo | Clo |
| | | | 1/2 | Cle | Cle | Cle | Clo | Clo |
| | | | 1/5 | Cle | Cle | Cle | Clo | Clo |

TABLE 6

Appearance of solutions comprising the nonionic surfactant composition (T2) in the presence of the compositions $(X_0)$, $(X_1)$, $(X_2)$, $(X_3)$ and $(X_4)$ at 20° C. (Cle: Clear; Clo: Cloudy)

| | | | | Appearance of the compositions | | | | |
|---|---|---|---|---|---|---|---|---|
| | | | | $X_0$ | $X_1$ | $X_2$ | $X_3$ | $X_4$ |
| Amount by weight of sodium hydroxide (% by weight) | 10% | Weight ratio (T2/Xi) | 1/1 | Cle | Clo | Cle | Cle | Clo |
| | | | 1/2 | Cle | Cle | Cle | Cle | Cle |
| | | | 1/5 | Cle | Cle | Cle | Cle | Cle |
| | 20% | Weight ratio (T2/Xi) | 1/1 | Cle | Clo | Clo | Clo | Clo |
| | | | 1/2 | Cle | Cle | Clo | Clo | Clo |
| | | | 1/5 | Cle | Cle | Cle | Cle | Clo |
| | 48% | Weight ratio (T2/Xi) | 1/1 | Cle | Clo | Clo | Clo | Clo |
| | | | 1/2 | Cle | Clo | Clo | Clo | Clo |
| | | | 1/5 | Cle | Cle | Cle | Cle | Clo |

TABLE 7

Appearance of solutions comprising the nonionic surfactant composition (T3) in the presence of the compositions $(X_0)$, $(X_1)$, $(X_2)$, $(X_3)$ and $(X_4)$ at 20° C. (Cle: Clear; Clo: Cloudy)

| | | | | Appearance of the compositions | | | | |
|---|---|---|---|---|---|---|---|---|
| | | | | $X_0$ | $X_1$ | $X_2$ | $X_3$ | $X_4$ |
| Amount by weight of sodium hydroxide (% by weight) | 10% | Weight ratio (T3/Xi) | 1/1 | Cle | Clo | Cle | Cle | Clo |
| | | | 1/2 | Cle | Cle | Cle | Cle | Cle |
| | | | 1/5 | Cle | Cle | Cle | Cle | Cle |
| | 48% | Weight ratio (T3/Xi) | 1/1 | Cle | Clo | Cle | Cle | Clo |
| | | | 1/2 | Cle | Clo | Cle | Cle | Clo |
| | | | 1/5 | Cle | Cle | Cle | Cle | Clo |

TABLE 8

Appearance of solutions comprising the nonionic surfactant composition (T4) in the presence of the compositions $(X_0)$, $(X_1)$, $(X_2)$, $(X_3)$ and $(X_4)$ at 20° C. (Cle: Clear; Clo: Cloudy)

| | | | | Appearance of the compositions | | | | |
|---|---|---|---|---|---|---|---|---|
| | | | | $X_0$ | $X_1$ | $X_2$ | $X_3$ | $X_4$ |
| Amount by weight of sodium hydroxide (% by weight) | 10% | Weight ratio (T4/Xi) | 1/1 | Cle | Clo | Clo | Clo | Clo |
| | | | 1/2 | Cle | Cle | Cle | Cle | Cle |
| | | | 1/5 | Cle | Cle | Cle | Cle | Clo |
| | 20% | Weight ratio (T4/Xi) | 1/1 | Cle | Clo | Clo | Clo | Clo |
| | | | 1/2 | Cle | Cle | Cle | Clo | Clo |
| | | | 1/5 | Cle | Cle | Cle | Cle | Clo |
| | 48% | Weight ratio (T4/Xi) | 1/1 | Cle | Clo | Clo | Clo | Clo |
| | | | 1/2 | Cle | Clo | Clo | Clo | Clo |
| | | | 1/5 | Cle | Cle | Cle | Clo | Clo |

Analysis of the Results

The comparison between the solubilizing performance levels observed for the compositions characterized by a low foaming power, namely the composition $(X_0)$, the composition $(X_1)$ and the composition $(X_4)$, shows that whatever the amount of sodium hydroxide present in the alkaline detergent solution prepared, the composition $(X_0)$ comprising n-heptylpolyglucosides which are subjects of the present invention is characterized by a solubilizing power which is greater than that observed with the composition $(X_1)$. The comparison between the solubilizing performance levels observed for the composition $(X_0)$ and for the composition $(X_2)$ shows that the composition $(X_0)$ is characterized by a greater solubilizing power than that of the composition $(X_2)$.

1.4.2—Evaluation of the Solubilizing Power in a Sodium Medium by Determining the Minimum Amount of Solubilization Composition to Make Soluble a Fixed Amount of Surfactants to be Made Soluble 1.4.2.1—Principle of the Method The object of this method is to determine the solubilizing power of a surfactant composition in a sodium medium for a nonionic surfactant insoluble in a sodium medium which is fixed, compared with surfactant compositions of the prior art.

In this method, the amount of nonionic surfactant insoluble in a sodium medium is fixed at 5% per 100% of the weight of each aqueous sodium medium selected, and the experimenter determines, by gradually adding the solubilizing surfactant composition, the minimum amount thereof to obtain a clear sodium solution. The method is carried out for the compositions according to the invention and for surfactant compositions of the prior art.

1.4.2.2—Experimental Protocol

An amount of 5 grams of the nonionic surfactant (Ti) to be made soluble and an amount of 95 grams of a mixture consisting of distilled water and of $y_1$ grams of sodium hydroxide are introduced into a 120 cm$^3$ glass flask.

A magnetized magnetic bar is placed in the glass flask, which is then magnetically stirred at a speed of 100 revolutions/minute for a period of 1 hour at a temperature of 20° C.

The solubilizing surfactant composition (Xi) to be tested is then subsequently gradually introduced and the experimenter determines the minimum amount of $x_1$ gram of said solubilizing surfactant composition (Xi) necessary to obtain a clear aqueous sodium solution.

1.4.2.3—Expression of the Results

When the visual appearance of the solution obtained according to the protocol of section 1.4.2.2 of the present application is clear, the experimenter notes the amount $x_1$ of the solubilizing surfactant composition (Xi) added in order to achieve this clear appearance.

1.4.2.4—Characterization of the Solubilizing Power in a Sodium Medium of the Composition ($X_0$) Comprising the Compounds of Formula (I) According to the Invention Compared with that of the Compositions ($X_1$), ($X_2$) and ($X_3$) Comprising the Prior Art Compounds Results Obtained The experimental protocol described in section 1.4.2.2 of the present application was carried out for the solubilizing surfactant compositions ($X_0$), ($X_1$), ($X_2$) and ($X_3$) and for the nonionic surfactant compositions (T5) and (T6) as described below:
- composition of polyethoxylated alcohols (T5), prepared by reaction between 1 molar equivalent of a mixture comprising, for 100% of its weight, 50% by weight of n-octanol and 50% by weight of n-decanol, and 4 molar equivalents of ethylene oxide in the presence of potassium hydroxide as basic catalyst,
- composition of polyethoxylated alcohols (T6), prepared by reaction between 1 molar equivalent of a mixture comprising, for 100% of its weight, a 85% by weight of n-decanol and 15% by weight of n-dodecanol, and 4 molar equivalents of ethylene oxide in the presence of potassium hydroxide as basic catalyst.

The experimental measurements were carried out according to the experimental protocol described in section 1.4.2.2 in the presence of different amounts $y_1$ of sodium hydroxide so as to obtain sodium hydroxide contents by weight of 10% and of 40% for each of the compositions (T5) and (T6).

The minimum amounts of the compositions ($X_0$), ($X_1$), ($X_2$) and ($X_3$) required to obtain a clear solution were noted by the experimenter and set out in table 9 below.

TABLE 9

Minimum amounts of compositions ($X_0$), ($X_1$), ($X_2$) and ($X_3$) required to make soluble sodium solutions comprising the nonionic surfactant compositions (T5) and (T6) at 20° C.

| Composition (Ti) to be made soluble | Amount of sodium hydroxide | Minimum amount of composition (Xi) in grams to obtain a clear solution according to the protocol described in section 1.4.2.2 | | | |
|---|---|---|---|---|---|
| | | $X_0$ | $X_1$ | $X_2$ | $X_3$ |
| (T5) | 10% | 3.3 g | 3.8 g | 4.1 g | 4.9 g |
| | 40% | 7.6 g | 13.0 g | 9.3 g | 12.4 g |
| (T6) | 10% | 3.02 g | 3.62 g | 3.53 g | 4.16 g |
| | 40% | 6.70 g | 12.79 g | 9.20 g | 10.92 g |

Analysis of the Results

Comparison between the solubilizing performance levels observed for the compositions characterized by a low foaming power, namely the composition ($X_0$) and the composition ($X_1$), shows that whatever the amount of sodium hydroxide present in the alkaline detergent solution prepared, the composition ($X_0$) comprising n-heptylpolyglucosides which are subjects of the present invention is characterized by a greater solubilizing power than that observed with the composition ($X_1$). The comparison between the solubilizing performance levels observed for the composition ($X_0$) and for the composition ($X_2$) shows that the composition ($X_0$) is characterized by a greater solubilizing power than that of the composition ($X_2$).

1.5) Evaluation of the Solubilizing Properties of n-heptylpolyglucosides in an Electrolytic Medium The solubilizing properties in an electrolytic medium of the composition ($X_0$) of n-heptylpolyglucosides, obtained according to the process previously described, were evaluated in comparison with the prior art compositions ($X_1$), ($X_2$), ($X_3$) and ($X_4$) as previously described, according to the evaluation methods described below for various nonionic surfactants and at various concentrations of sodium metasilicate.

1.5.1)—Evaluation of the Solubilizing Power in an Electrolytic Medium for Several Weight Ratios of Surfactants to be Made Soluble/Solubilizing Composition 1.5.1.1—Principle of the Method The object of this method is to determine the solubilizing power of a surfactant composition in an electrolytic medium for a nonionic surfactant insoluble in an electrolytic medium which is fixed, compared with surfactant compositions of the prior art.

1.5.1.2—Experimental Protocol

An amount of one gram of the nonionic surfactant (Ti) to be made soluble, an amount of $x_2$ gram of the solubilizing surfactant composition (Xi) to be tested, an amount of $y_2$ grams of sodium metasilicate and an amount of distilled water to make up the volume to obtain a solution of 100 cm$^3$ are introduced into a 120 cm$^3$ glass flask. A magnetized magnetic bar is placed in the glass flask, which is then magnetically stirred at a speed of 100 revolutions/minute for a period of 1 hour at a temperature of 20° C.

1.5.2.3—Expression of the Results

The visual appearance of the solution obtained according to the protocol of section 1.5.1.2 of the present application is noted by the experimenter and described as "clear" or "cloudy", as appropriate.

1.5.1.4—Characterization of the Solubilizing Power in an Electrolytic Medium of the Composition ($X_0$) Comprising the Compounds of Formula (I) According to the Invention Compared with that of the Compositions $(X_1)$, $(X_2)$, $(X_3)$ and $(X_4)$ Comprising the Prior Art Compounds Results Obtained The experimental protocol described in section 1.5.1.2 of the present application was carried out for the solubilizing surfactant compositions $(X_0)$, $(X_1)$, $(X_2)$, $(X_3)$ and $(X_4)$ and for the nonionic surfactant compositions (T1), (T2), (T3) and (T4), as previously described.

The experimental measurements were carried out in the presence of different amounts $y_2$ of sodium metasilicate so as to obtain contents by weight of 10%, 20% and 30% for each of the amounts $x_2$ of the various solubilizing compositions $(X_1)$, $(X_2)$, $(X_3)$ and $(X_4)$ tested, and for each of the nonionic surfactants (T1), (T2), (T3) and (T4) described above. The amount $x_2$ of the various solubilizing compositions $(X_1)$, $(X_2)$, $(X_3)$ and $(X_4)$ tested is determined so as to achieve weight ratios of composition (Ti)/compositions (Xi) equal to 1/1, to 1/2 and to 1/5.

TABLE 10

Appearance of solutions comprising the nonionic surfactant composition (T1) in the presence of the compositions $(X_0)$, $(X_1)$, $(X_2)$, $(X_3)$ and $(X_4)$ at 20° C. (Cle: Clear; Clo: Cloudy)

| Amount by weight of sodium metasilicate | Weight ratio composition (T1)/compositions (Xi) | Appearance observed | | | | |
|---|---|---|---|---|---|---|
| | | $(X_0)$ | $(X_1)$ | $(X_2)$ | $(X_3)$ | $(X_4)$ |
| 10% | 1/1 | Cle | Clo | Clo | Clo | Clo |
| | 1/2 | Cle | Cle | Cle | Cle | Cle |
| | 1/5 | Cle | Cle | Cle | Cle | Cle |
| 20% | 1/1 | Cle | Clo | Clo | Clo | Clo |
| | 1/2 | Cle | Cle | Clo | Clo | Cle |
| | 1/5 | Cle | Cle | Cle | Cle | Cle |
| 30% | 1/1 | Cle | Clo | Clo | Clo | Clo |
| | 1/2 | Cle | Clo | Clo | Clo | Clo |
| | 1/5 | Cle | Clo | Clo | Clo | Clo |

TABLE 11

Appearance of solutions comprising the nonionic surfactant composition (T2) in the presence of the compositions $(X_0)$, $(X_1)$, $(X_2)$, $(X_3)$ and $(X_4)$ at 20° C. (Cle: Clear; Clo: Cloudy)

| Amount by weight of sodium metasilicate | Weight ratio composition (T2)/compositions (Xi) | Appearance observed | | | | |
|---|---|---|---|---|---|---|
| | | $(X_0)$ | $(X_1)$ | $(X_2)$ | $(X_3)$ | $(X_4)$ |
| 10% | 1/1 | Cle | Clo | Cle | Cle | Cle |
| | 1/2 | Cle | Cle | Cle | Cle | Cle |
| | 1/5 | Cle | Cle | Cle | Cle | Cle |
| 20% | 1/1 | Cle | Clo | Clo | Clo | Clo |
| | 1/2 | Cle | Cle | Cle | Cle | Cle |
| | 1/5 | Cle | Cle | Cle | Cle | Cle |
| 30% | 1/1 | Cle | Clo | Clo | Clo | Clo |
| | 1/2 | Cle | Clo | Clo | Clo | Clo |
| | 1/5 | Cle | Clo | Clo | Clo | Clo |

TABLE 12

Appearance of solutions comprising the nonionic surfactant composition (T3) in the presence of the compositions $(X_0)$, $(X_1)$, $(X_2)$, $(X_3)$ and $(X_4)$ at 20° C. (Cle: Clear; Clo: Cloudy)

| Amount by weight of sodium metasilicate | Weight ratio composition (T3)/compositions (Xi) | Appearance observed | | | | |
|---|---|---|---|---|---|---|
| | | $(X_0)$ | $(X_1)$ | $(X_2)$ | $(X_3)$ | $(X_4)$ |
| 10% | 1/1 | Cle | Clo | Cle | Cle | Cle |
| | 1/2 | Cle | Cle | Cle | Cle | Cle |
| | 1/5 | Cle | Cle | Cle | Cle | Cle |
| 30% | 1/1 | Cle | Clo | Clo | Clo | Clo |
| | 1/2 | Cle | Clo | Clo | Clo | Clo |
| | 1/5 | Cle | Clo | Clo | Clo | Clo |

TABLE 13

Appearance of solutions comprising the nonionic surfactant composition (T4) in the presence of the compositions $(X_0)$, $(X_1)$, $(X_2)$, $(X_3)$ and $(X_4)$ at 20° C. (Cle: Clear; Clo: Cloudy)

| Amount by weight of sodium metasilicate | Weight ratio composition (T4)/compositions (Xi) | Appearance observed | | | | |
|---|---|---|---|---|---|---|
| | | $(X_0)$ | $(X_1)$ | $(X_2)$ | $(X_3)$ | $(X_4)$ |
| 10% | 1/1 | Cle | Clo | Cle | Cle | Cle |
| | 1/2 | Cle | Clo | Cle | Cle | Clo |
| | 1/5 | Cle | Clo | Cle | Cle | Clo |
| 20% | 1/1 | Cle | Clo | Clo | Clo | Cle |
| | 1/2 | Cle | Clo | Clo | Clo | Clo |
| | 1/5 | Cle | Clo | Cle | Clo | Clo |
| 30% | 1/1 | Cle | Clo | Clo | Clo | Clo |
| | 1/2 | Cle | Clo | Clo | Clo | Clo |
| | 1/5 | Cle | Clo | Clo | Clo | Clo |

Analysis of the Results Obtained

The comparison between the solubilizing performance levels observed for the compositions characterized by a low foaming power, namely the composition $(X_0)$, the composition $(X_1)$ and the composition $(X_4)$, shows that for an amount of 10% by weight of sodium silicate, a single equivalent by weight of composition $(X_0)$ is required to obtain a clear alkaline detergent solution for all the nonionic surfactant compositions (T1), (T2), (T3) and (T4), contrary to the other compositions.

The comparison between the solubilizing performance levels observed for the composition $(X_0)$ and for the composition $(X_2)$ shows that, for an amount of sodium silicate present in a proportion of 30% by weight in the alkaline detergent composition, use of 5 equivalents by weight of the composition $(X_2)$ does not manage to make the nonionic surfactant compositions (T1), (T2), (T3) and (T4) soluble, whereas a single equivalent by weight of the composition $(X_0)$ is required to make the nonionic surfactant compositions (T1), (T2), (T3) and (T4) soluble.

1.5.2—Evaluation of the Solubilizing Power in an Electrolytic Medium by Determining the Minimum Amount of Solubilizing Composition to Make Soluble a Fixed Amount of Surfactants to be Made Soluble 1.5.2.1—Principle of the Method The object of this method is to determine the solubilizing power of a surfactant composition in an electrolytic medium for a nonionic surfactant insoluble in an electrolytic medium which is fixed, compared with surfactant compositions of the prior art.

In this method, the amount of nonionic surfactant insoluble in an electrolytic medium is fixed at 5% for 100% of the weight of each aqueous electrolytic medium selected, and the experimenter determines, by gradually adding the solubilizing surfactant composition, the minimum amount thereof to obtain a clear electrolytic solution. The method is carried out for the compositions according to the invention and for surfactant compositions of the prior art.

1.5.2.2—Experimental Protocol

An amount of 5 grams of the nonionic surfactant (Ti) to be made soluble and an amount of 95 grams of a mixture consisting of distilled water and of an amount of $y_2$ grams of sodium metasilicate are introduced into a 120 cm³ glass flask.

A magnetized magnetic bar is placed in the glass flask, which is then magnetically stirred at a speed of 100 revolutions/minute for a period of 1 hour at a temperature of 20° C.

The solubilizing surfactant composition (Xi) to be tested is then gradually introduced and the experimenter determines the minimum amount of $x_1$ gram of said solubilizing surfactant composition (Xi) required to obtain a clear aqueous electrolytic solution.

1.5.2.3—Expression of the Results

When the visual appearance of the solution obtained according to the protocol of section 1.5.2.2 of the present application is clear, the experimenter notes the amount $x_1$ of the solubilizing surfactant composition (Xi) added to achieve this clear appearance.

1.5.2.4—Characterization of the Solubilizing Power in an Electrolytic Medium of the Composition ($X_0$) Comprising the Compounds of Formula (I) According to the Invention Compared with that of the Compositions ($X_1$), ($X_2$) and ($X_3$) Comprising the Prior Art Compounds Results Obtained The experimental protocol described in section 1.5.2.2 of the present application was carried out for the solubilizing surfactant compositions ($X_0$), ($X_1$), ($X_2$) and ($X_3$) and for the nonionic surface compositions (T5) and (T6) as previously described.

The experimental measurements were carried out according to the experimental protocol described in section 1.5.2.2 in the presence of different amounts $y_2$ of sodium metasilicate so as to obtain contents by weight of sodium metasilicate of 10% and 20% for each of the compositions (T5) and (T6).

The minimum amounts of the compositions ($X_0$), ($X_1$), ($X_2$) and ($X_3$) required to obtain a clear solution were noted by the experimenter and set out in table 14 below.

TABLE 14

Minimum amounts of compositions ($X_0$), ($X_1$), ($X_2$) and ($X_3$) required to make soluble electrolytic solutions comprising the nonionic surfactant compositions (T5) and (T6) at 20° C.

| Composition (Ti) to be made soluble | Amount of sodium metasilicate | Minimum amount of composition (Xi) in grams to obtain a clear solution according to the protocol described in section 1.5.2.2 | | | |
|---|---|---|---|---|---|
| | | $X_0$ | $X_1$ | $X_2$ | $X_3$ |
| (T5) | 10% | 2.39 g | 3.70 g | 2.76 g | 2.92 g |
| | 20% | 4.13 g | 5.04 g | 6.80 g | 6.08 g |
| (T6) | 10% | 2.77 g | 4.19 g | 3.20 g | 3.60 g |
| | 20% | 3.84 g | 4.78 g | 6.17 g | 6.84 g |

Analysis of the Results Obtained

The comparison between the solubilizing performance levels observed for the compositions characterized by a low foaming power, namely the composition ($X_0$) and the composition ($X_1$), shows that, whatever the amount of sodium metasilicate present in the detergent solution prepared, the composition ($X_0$) comprising n-heptylpolyglucosides which are subjects of the invention is characterized by a greater solubilizing power than that observed for the composition ($X_1$), since the minimum amount required to obtain a clear solution is less for the composition ($X_0$) than for the composition ($X_1$).

The comparison between the solubilizing performance levels observed for the composition ($X_0$) and for the compositions ($X_2$) and ($X_3$) shows that, whatever the amount of sodium metasilicate present in the detergent solution prepared, the composition ($X_0$) comprising n-heptylpolyglucosides which are subjects of the present invention is characterized by a greater solubilizing power than that observed for the compositions ($X_2$) and ($X_3$), since the minimum amount required to obtain a clear solution is less for the composition ($X_0$) than for the compositions ($X_2$) and ($X_3$).

1.6) Conclusions

The composition ($X_0$) comprising n-heptylpolyglucosides which are subjects of the present invention shows improved low-foaming and solubilizing properties, in an alkaline and electrolytic medium, even in high proportions, compared with the solubilizing agents known in the prior art.

2) Aqueous Alkaline Detergent Compositions 2.1. Industrial Cleaning Product for Floors 2.1.1 Preparation of the Industrial Cleaning Composition for Floors

| Ingredients | Content by weight |
|---|---|
| Simulsol ™ NW 900[1] | 5% |
| Composition ($X_0$) | 4% |
| Dowanol ™ DPM[2] | 2% |
| D-Limonene | 3% |
| Sodium gluconate | 5% |
| Dequest ™ 3000S[3] | 2% |
| 5% sodium hydroxide solution | qs pH = 13 |
| Water | qs 100% |
| Fragrance | qs |
| Dye | qs |

[1]Simulsol ™ NW 900: detergent surfactant composition sold by the company SEPPIC, comprising polyethoxylated alcohols resulting from the reaction of one molar equivalent of an alcohol sold under the brand name Exxal ™ 10 with 9 molar equivalents of ethylene oxide.
[2]Dowanol ™ DPM: dipropylene glycol monomethyl ether sold by the company Dow Chemicals
[3]Dequest ™ 3000 S: sodium phosphonate sold by the company Monsanto Procedure for preparing the alkaline detergent composition: each ingredient is successively introduced into a mixing tank with moderate mechanical stirring, at ambient temperature, until a homogenous and clear composition is obtained. The stirring is maintained for 30 minutes at 20° C. and then the dye and the fragrance are introduced. The composition obtained has a pH measured at 12.9, and remains clear and homogeneous after storage for a period of one month at 40° C. and clear and homogeneous after storage for a period of one month at 5° C.

2.1.2 Cleaning Process Using the Composition Prepared in 2.1.1:

A dilution to 10% in water of the composition prepared in 2.1.1 is prepared at ambient temperature, and then applied to a tiled floor soiled with dirt made up of oil and grease, by means of floor cleaning machine. The floor thus impregnated with the composition prepared in 2.1.1 is then rinsed with hot water (60° C.) under pressure by means of a garden hose.

2.2. Cleaning Composition for Cars and Trucks
2.2.1 Preparation of the Cleaning Composition for Cars and Trucks

| Ingredients | Content by weight |
| --- | --- |
| Simulsol™ OX1006L[(4)] | 5% |
| Composition ($X_0$) | 5% |
| Dowanol™ DPM[(2)] | 5% |
| Sodium gluconate | 5% |
| Anhydrous sodium metasilicate | 0.3% |
| Solid potassium hydroxide | qs pH = 12 |
| Sodium nitrilotriacetate | 5% |
| Water | qs 100% |
| Fragrance | qs |
| Dye | qs |

[(4)]Simulsol™ OX1006L: detergent surfactant composition sold by the company SEPPIC, comprising polyethoxylated alcohols resulting from the reaction of one molar equivalent of an alcohol sold under the brand name Exxal™ 10 with 6 molar equivalents of ethylene oxide.

Procedure for preparing the cleaning composition for cars and trucks: each ingredient is successively mixed into a mixing tank with vigorous mechanical stirring, at ambient temperature, until a homogeneous and clear composition is obtained. The stirring is maintained for 30 minutes at 20° C. and then the dye and the fragrance are introduced. The composition obtained has a pH measured at 12.1, and remains clear and homogeneous after storage for a period of one month at 20° C.

2.2.2 Cleaning Process Using the Composition Prepared in 2.2.1:

A dilution to 10% in water of the composition prepared in 2.1.1 is prepared at ambient temperature, and then applied at a temperature of 60° C. to the bodywork of a motor vehicle soiled with mud and grease, by means of a garden hose at low pressure. The vehicle impregnated with the dilution of the cleaning composition prepared in 2.2.1 is rinsed with water at 60° C. under high pressure (100 bar). The vehicle thus cleaned no longer has any dirt on its sides and has a shiny appearance.

2.2.3 Cleaning of Aluminum Wheels of Cars or of Trucks

The cleaning process described in 2.2.2 is used to clean aluminum wheels of cars or of trucks soiled with oil and grease, but using a dilution to 15% by weight in water of the composition prepared in 2.2.1.

2.3 Cleaning Composition for Ovens and Cooking Grills
2.3.1 Preparation of the Cleaning Composition for Ovens and Cooking Grills

| Ingredients | Content by weight |
| --- | --- |
| Simulsol™ OX1309L[(5)] | 2% |
| Composition ($X_0$) | 2% |
| Solagum™ SF 306[(6)] | 6% |
| 100% sodium hydroxide | 25% |
| Water | qs 100% |

[(5)]Simulsol™ OX1309L: detergent surfactant composition sold by the company SEPPIC, comprising polyethoxylated alcohols resulting from the reaction of one molar equivalent of an alcohol sold under the brand name Exxal™ 13 with 9 molar equivalents of ethylene oxide.
[(6)]Solagum™ SF 306: thickening composition provided in the form of a water-in-oil emulsion and comprising a crosslinked polymer based on acrylamide and on the sodium salt of 2-acrylamido-2-methylpropanesulfonate.

Procedure for Preparing the Cleaning Composition for Ovens and Cooking Grills:

a) A pregel is prepared at 20° C. by adding the Simulsol™ OX1309L and then the composition ($X_0$) according to the invention to water. The Solagum™ SF 306 is then introduced into the aqueous solution and mixed until a gel of stable viscosity is obtained.

b) The sodium hydroxide is then gradually introduced with mechanical stirring at a temperature of 20° C. until a homogeneous gel is obtained.

The gel obtained at the end of step b) shows a homogeneous and clear appearance, with a viscosity of 11 000 mPa·s (measured using a Brookfield LVT viscometer, at a speed of 6 revolutions/minute). After a storage period of 6 months at 25° C., the gel obtained at the end of step b) of this procedure has a homogeneous and clear appearance, with a viscosity of 12 000 mPa·s (measured using a Brookfield LVT viscometer, at a speed of 6 revolutions/minute).

2.3.2 Cleaning Process Using the Composition Prepared in 2.3.1:

The composition prepared in 2.3.1, provided in the form of a gel, is sprayed at ambient temperature onto the walls of an oven soiled with food fats and onto the cooking grills also soiled with food fats. After a period of 10 minutes, the oven walls and the cooking grills are rinsed with hot water at 60° C. The oven walls and the surfaces of the cooking grills thus cleaned no longer show any soiling.

The invention claimed is:

1. A composition ($C_1$) comprising, for 100% of its weight:
   a) from 0.5% to 20% by weight of at least one compound of formula (I) $nC_7H_{15}$—O-$(G)_p$-H (I);
   b) from 0.5% to 80% by weight of at least one nonionic surfactant of formula (II):

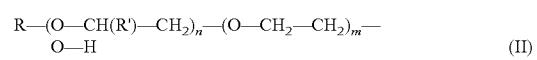
   $$R-(O-CH(R')-CH_2)_n-(O-CH_2-CH_2)_m-O-H \quad (II)$$

in which R represents a linear or branched, saturated or unsaturated, hydrocarbon-based aliphatic radical comprising from 8 to 14 carbon atoms, R' represents a methyl or propyl radical, n represents an integer greater than or equal to 0 and less than or equal to 15, m represents an integer greater than or equal to 0 and less than or equal to 15, it being understood that the sum n+m is greater than zero;
   c) from 10% to 50% by weight of at least one alkaline agent chosen from the elements of the group made up of alkali metal hydroxides and alkaline-earth metal hydroxides;
   d) from 15% to 89% by weight of water; and, optionally
   e) from 10% to 50% by weight of at least one water softening agent.

2. The composition ($C_1$) as defined in claim 1, characterized in that the weight ratio between the compound of formula (II) and the compound of formula (I) is less than or equal to 9/1 and greater than or equal to 1/4.

* * * * *